United States Patent
Wang et al.

(10) Patent No.: US 7,447,597 B2
(45) Date of Patent: Nov. 4, 2008

(54) DATA PROCESSING/VISUALIZATION METHOD FOR TWO (MULTI) DIMENSIONAL SEPARATION GAS CHROMATOGRAPHY XMASS SPECTROMETRY (GCXMS) TECHNIQUE WITH A TWO (MULTIPLY) DIMENSIONAL SEPARATION CONCEPT AS AN EXAMPLE

(75) Inventors: Frank C. Wang, Annandale, NJ (US);
Kuangnan Qian, Belle Meade, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 372 days.

(21) Appl. No.: 11/409,448

(22) Filed: Apr. 21, 2006

(65) Prior Publication Data
US 2006/0265141 A1    Nov. 23, 2006

Related U.S. Application Data

(60) Provisional application No. 60/678,728, filed on May 6, 2005.

(51) Int. Cl.
G06F 19/00 (2006.01)
G06F 17/40 (2006.01)
G01N 37/00 (2006.01)
G01N 30/00 (2006.01)

(52) U.S. Cl. ............... 702/32; 73/19.01; 73/23.2; 73/23.35; 73/31.07; 73/53.01; 436/43; 702/19; 702/22; 702/189

(58) Field of Classification Search ............... 73/19.01, 73/19.02, 23.2, 23.35, 25.01, 31.07, 53.01, 73/863, 863.21; 340/500; 436/43; 702/1, 702/19, 22, 23, 24, 25, 26, 27, 28, 29, 30, 702/32, 127, 189
See application file for complete search history.

(56) References Cited

U.S. PATENT DOCUMENTS

| | | | | |
|---|---|---|---|---|
| 4,008,388 A * | 2/1977 | McLafferty et al. | ............ | 702/27 |
| 4,353,242 A * | 10/1982 | Harris et al. | ............... | 73/23.36 |
| 4,507,555 A * | 3/1985 | Chang | ......................... | 250/281 |
| 5,175,430 A * | 12/1992 | Enke et al. | ................... | 250/282 |
| 5,699,269 A * | 12/1997 | Ashe et al. | ..................... | 702/30 |
| 5,744,702 A * | 4/1998 | Roussis et al. | ............. | 73/53.01 |
| 5,777,205 A * | 7/1998 | Nakagawa et al. | ......... | 73/24.02 |
| 5,905,195 A * | 5/1999 | Roussis et al. | ............. | 73/53.01 |
| 6,107,627 A * | 8/2000 | Nakagawa et al. | .......... | 250/292 |
| 6,646,255 B2 * | 11/2003 | Fukuda | ........................ | 250/288 |
| 2002/0074491 A1 * | 6/2002 | Fukuda | ........................ | 250/288 |
| 2005/0009114 A1 * | 1/2005 | Korbling et al. | ............. | 435/7.2 |
| 2005/0092910 A1 * | 5/2005 | Geromanos et al. | ......... | 250/282 |
| 2008/0070314 A1 * | 3/2008 | Geromanos et al. | ........... | 436/86 |
| 2008/0135744 A1 * | 6/2008 | Geromanos et al. | ......... | 250/281 |
| 2008/0142696 A1 * | 6/2008 | Geromanos et al. | ......... | 250/282 |

* cited by examiner

Primary Examiner—Edward R Cosimano
(74) Attorney, Agent, or Firm—Paul E. Purwin (57) ABSTRACT

This invention is a data processing/visualization method which includes the software development and operation to apply to any multi-dimensional separation. The GC-MS analysis of diesel is an example to demonstrate this software development and operation. The steps of this method includes (1) displaying the total ion chromatogram obtained from a GC-MS experiment, (2) displaying each mass spectrum versus retention time, (3) selecting a normal paraffin family as the reference compound family for relative polarity display, (4) transforming every mass slice to line-up normal paraffin compound family in the same relative retention time (position), (5) rotating the axis to best display the two (multi) dimensional data.

13 Claims, 6 Drawing Sheets

DATA PROCESSING/VISUALIZATION METHOD FOR TWO (MULTI) DIMENSIONAL SEPARATION GAS CHROMATOGRAPHY XMASS SPECTROMETRY (GCXMS) TECHNIQUE WITH A TWO (MULTIPLY) DIMENSIONAL SEPARATION CONCEPT AS AN EXAMPLE

This application claims the benefit of U.S. Provisional application 60/678,728 filed May 6, 2005, now expired.

BACKGROUND OF THE INVENTION

The present invention is a method for data processing and visualization of a multi-dimensional separation. The chromatogram from a gas chromatography, mass spectrometry system has been used as a typical example to demonstrate the data processing and visualization method.

Gas Chromatography hyphenated (combined) with Mass Spectrometry, GC-MS, has become a powerful technique for separation/identification of unknown components over many years. In this hyphenation, the GC performs separation and MS performs in separated component identification. For complex mixture such as a petroleum stream, this technique, similar to traditional GC, still suffers a lot of co-elution of components in the GC separation and many mixed mass spectra (caused by co-elution) that create difficulty for MS interpretation.

If one applies the two (multiple) dimensional separation concept to GC-MS to create a data processing/visualization method, GC-MS not only can be used as a separation/identification tool, but also a two (multiple) dimensional separation device, GC×MS. This new data processing/visualization method greatly improves the separation of complex mixture by this Gas Chromatography hyphenated with Mass Spectrometry technique. The co-elution problem in the traditional GC separation when analyze a complex mixture can be reduced in a great extent.

The two (multiple) dimensional separation has been introduced nearly ten years. The separation technology development to carry out this two (multiple) dimensional separation concept is almost all focus on the chromatographic type development. However, multi-dimensional chromatographic separation can be extended to other types of separation techniques. Other separations, such as mass separation by mass spectrometry (MS), wavelength/internal atomic/molecular motion separation by ultraviolet (UV), visible (VIS), and infrared (IR) spectrometer and thermal separation by thermogravimeric analysis (TGA) techniques, all use different mechanisms of separation. When hyphenated with any of the techniques, a two (multiple) dimensional separation can be accomplished.

SUMMARY OF THE INVENTION

This invention is a data processing/visualization method which includes the software development and operation to apply to any multi-dimensional separation. The "chromatographic" type separation includes Gas Chromatography (GC), Liquid Chromatography (LC), Supercritical Fluid Chromatography (SFC), and Size Exclusion Chromatography (SEC), etc. The "non-chromatographic" type separation includes Ultraviolet-Visible Spectroscopy (UV-Vis), Infrared Spectroscopy (IR), Atomic Absorption and Emission Spectroscopy (AA and AES), Mass Spectroscopy (MS), and Nuclear Magnetic Resonance Spectroscopy (NMR), etc. The two-dimensional separation with at least one dimensional "non-chromatographic" type separation can be any combination of "chromatographic" type and "non-chromatographic" type or both "chromatographic" and "non-chromatographic" type combination. For example, GC-MS, LC-UV, SFC-UV, LC-IR, GC-IR, LC-NMR, etc. The GC-MS analysis of diesel is an example to demonstrate this software development and operation. The steps of the method of this example includes (1) determining the total ion chromatogram obtained from a GC-MS experiment, (2) determining each mass spectrum versus retention time, (3) selecting a normal paraffin family as the reference compound family for the relative polarity determination, (4) transforming every mass slice to line-up normal paraffin compound family in the same relative retention time (position), (5) rotate the axis to best display the two (multi) dimensional data.

If one applies the two (multiple) dimensional separation concept to GC-MS to create a data processing/visualization method, GC-MS not only can be used as a separation/identification tool, but also a two (multiple) dimensional separation device, GC×MS. The immediately benefit of GC×MS is that there is no change from the traditional GC-MS operation. There is only software enhancement to improve the data processing/visualization. One example is: when operate with a hyphenated GC-MS technique, where GC with a polar capillary column (can achieve the polarity separation) and MS with non-fragmentation ionization method (will enable the mass separation toward the boiling separation, higher mass approximately equivalent to higher boiling point), to analyze a complex mixture such as a petroleum stream, the two (multiple) dimensional separation can be achieved with this new data processing/visualization method.

The improvement of data processing/visualization can show boiling point type separation based on the molecular weight/mass as well as molecular class separation based on the molecular polarity. Because of the exact mass operation, the specific element containing compound distribution can also be generated through the extraction of specific mass groups. For qualitative analysis, GC×MS is a technique where one experiment can generate a wide range of information.

DETAILED DESCRIPTION OF THE PREFERRED EMBODIMENTS

The present invention is a method for the processing and display of a two (multi) dimensional data obtained from any two (multi) "chromatographic" or "non-chromatographic" type separation system. The invention includes the steps of appropriate determine the separation dimension from each separation technique, referencing compound class or compound family, transforming every other separated compound in different separation dimension to line-up to referencing compound class or family, and rearranging the separation dimension axis to best display the two (multi) dimensional separation results.

As described above, the multi-dimensional chromatographic separation can be extended to other types of separation techniques. Other separations, such as mass separation by mass spectrometry (MS), wavelength/internal atomic/molecular motion separation by ultraviolet (UV), visible (VIS), and infrared (IR) spectrometer and thermal separation by thermogravimeric analysis (TGA) techniques, all use different mechanisms of separation. When hyphenated with any of the techniques, a two (multiple) dimensional separation can be accomplished.

The separation dimension can be defined as follows:

For "chromatographic" type separation techniques that include gas chromatography (GC), liquid chromatography (LC), supercritical fluid chromatography (SFC), size exclusion chromatography (SEC), etc., the separation dimension is in retention time (minutes) or retention time related/deviated unit (such as temperature in GC, molecular solubility in LC, molecular weight in SEC, etc.).

For "non-chromatographic" type techniques such as various spectroscopic/wavelength-type separation techniques, that include X-ray, Vacuum ultraviolet (VUV), ultraviolet and visible (UV-Vis), infrared (IR), atomic absorption (AA) and atomic emission spectroscopy (AES), Fluorescence, the separation dimension can be defined as: in wavelength (length unit, such as nanometer (nm), angstrom (Å), or wavenumber ($cm^{-1}$), etc. or wavelength related/deviated unit (such as energy unit, electron volts, (eV), etc.

For "non-chromatographic" type techniques such as mass separation techniques, that include Mass Spectrometry, the separation dimension can be defined as: mass or molecular weight (Mw) or mass/molecular weight related/deviated unit (such as temperature unit, degree C. or F., boiling point, etc.

For "non-chromatographic" type techniques such as thermal separation techniques, that include Thermalgravmetric analysis (TGA), differential scanning calorimeter (DSC), evolved gas analysis (EVA), and Pyrolysis (Py), the separation dimension can be defined as: temperature unit, degree C. or F.

The referencing compound class or family will depend on the purpose of two (multi) dimensional separation and the desired information obtained from the separation. The compound class and family can be defined as follows:

For "chromatographic" type separation techniques that include GC, LC, SFC, SEC, etc., the compound class or family is similar in structure, similar in polarity, or similar in other physical properties which the chromatographic separation technique is based on. The real example such as family of normal paraffins, family of linear alkyl benzene, family of linear alkyl naphthalene, or family of saturated straight chain fatty acid, etc.

For "non-chromatographic" type techniques such as various spectroscopic/wavelength-type separation techniques, that include X-ray, Vacuum ultraviolet (VUV), ultraviolet and visible (UV-Vis), infrared (IR), atomic absorption (AA) and atomic emission spectroscopy (AES), Fluorescence, the compound class or family is similar in structure, similar in energy being absorbed, or similar in other intra-inter atomic and molecular energy level transition which the spectroscopic separation technique is based on. The real example such as family of molecules with the same functional group like alpha-olefin family, family of straight chain alcohol, family of one-ring aromatics with the same ring position substitution, or family of compounds with hydrogen bonding, etc.

For "non-chromatographic" type techniques such as mass separation techniques, that include Mass Spectrometry, the compound class or family is similar in molecular structure, similar in certain functional group in the structure, which the mass spectrometric separation technique is based on. The real example such as family of paraffins, family of olefins, family of one-ring aromatics, or family of dibenzothiophenes, etc.

For "non-chromatographic" type techniques such as thermal separation techniques, that include Thermalgravmetric analysis (TGA), DSC, evolved gas analysis (EVA), and Pyrolysis (Py), the compound class or family is similar in molecular structure, similar in certain functional group in the structure, which the thermal separation technique is based on. The real example such as family of paraffins, family of naphthenes, family of three-ring aromatics, or family of indoles, etc.

Gas Chromatography hyphenated with Mass Spectrometry, GC-MS, has become a powerful technique for separation/identification of unknown components over many years. In this hyphenation, the GC performs separation and MS performs in separated component identification. For complex mixture such as petroleum, this technique, similar to traditional GC, still suffers a lot of co-elution of components in the GC separation and many mixed mass spectra (caused by co-elution) that create difficulty for MS interpretation.

If one applies the two (multiple) dimensional separation concept to GC-MS to create a data processing/visualization method, GC-MS not only can be used as a separation/identification tool, but also a two (multiple) dimensional separation device, GC×MS. The immediately benefit of GC×MS is that there is no change from the traditional GC-MS operation. There is only software enhancement to improve the data processing/visualization. One example is: when operate with a hyphenated GC-MS technique, where GC with a polar capillary column (can achieve the polarity separation) and MS with non-fragmentation ionization method (will enable the mass separation toward the boiling separation, higher mass approximately equivalent to higher boiling point), to analyze a complex mixture such as a petroleum stream, the two (multiple) dimensional separation can be achieved with this new data processing/visualization method.

The improvement of data processing/visualization can show boiling point type separation based on the molecular weight/mass as well as molecular class separation based on the molecular polarity. Because of the exact mass operation, the specific element containing compound distribution can also be generated through the extraction of specific mass groups. For qualitative analysis, GC×MS is a technique where one experiment can generate a wide range of information.

EXAMPLE

A GC×MS experiment has been performed to demonstrate this new data processing/visualization method. During this exercise, figures are given to illustrate the uniqueness and advantages of this powerful data processing/visualization method.

Experimental Conditions

The GC system used is an Agilent 6890 gas chromatograph configured with inlet, and column. The detector is a mass spectrometer. The GC column used is a mid-polar column (BPX-50, 30 meter, 0.25 mm I.D., 0.25 μm film). This column separates petroleum molecules mainly by polarity.

About 1.0 μL of the sample was injected via a Split/Splitness (S/S) injector with a split ratio 50:1 at 300° C. in constant pressure mode at 45 p.s.i. at oven temperature 60° C. The oven was programmed from 60° C. with 0 minute hold and 5° C. per minute increment to 360° C. with 20 minute hold and with total run time 80 minutes.

After GC, a time-of-flight (TOF) mass spectrometer (MacroMass GCT, Waters Inc. Milford, Mass., USA) was used to perform the mass spectrometry analysis. In brief, the temperature of the GC-TOF interface was maintained at 350° C. Field Ionization (FI) was used to ionize diesel molecules eluting from the GC. The FI emitter (CarboTech, Gesellschaft für instrumentelle Analytik mbH, Germany) consists of a 10 μm tungsten wire onto which carbon microneedles have been grown. The FI emitter is carefully aligned with the end of the GC capillary column so that effluent molecules pass near the tips of the carbon dendrites. The emitter (at ground voltage) is about 1.5 mm away from a pair of extraction rods held at high potential (−12 kV), producing very high electric fields (~$10^{-7}$ to $10^{-8}$ V/cm) around the tips of the carbon dendrites. It is generally believed that under the influence of these fields, an electron can be removed from the molecule via quantum tunneling effects, generating radical molecular ions with minimal fragmentation. FI emitter current was typically set at 0 mA during scan. The emitter was flashed by a current of 12 mA during an inter-scan cycle (0.2 second) to regenerate the emitter.

Ions generated by FI were accelerated and focused into a pusher region of the TOF. A voltage pulse of 960 V is applied, ejecting ions orthogonal to the original ion path. The ion packet drifts through a TOF with an effective path length of 1.2 meter. A reflectron reflects ions back to a dual microchannel plate detector. Ion arrivals are recorded using a time to digital converter (TDC) with a sampling rate of 3.6 GHz. The voltage pulse was applied at a frequency of 30 kHz. A full spectrum was generated every 33 μS. The mass range was normally set at 50-800 Dalton. The scan duration time or spectrum accumulation time was one second (i.e. every "scan" is an accumulation of 30 thousands spectrum).

Since FI generates mostly a single molecular ion, a mixture of compounds (normally halogenated hydrocarbons) was used to calibrate a wide mass range from 50 to 800 Daltons. A typical calibration mixture contains heptacosapentafluorobenzene, hexafluorobenzene, pentafluoroiodobenzene, pentafluorochlorobenzene, perfluoro-trimethylcyclohexane, xylene and acetone. The calibrants were introduced into the ion source via a batch inlet and were pumped out after the calibration. During sample analyses, a single lock compound was introduced as an internal reference for accurate mass measurement. In our experiments, pentafluoroiodobenzene with a monoisotopic mass of 293.896 Daltons was used as the internal reference.

Data Processing/Visualization Method Development

Figure 1:
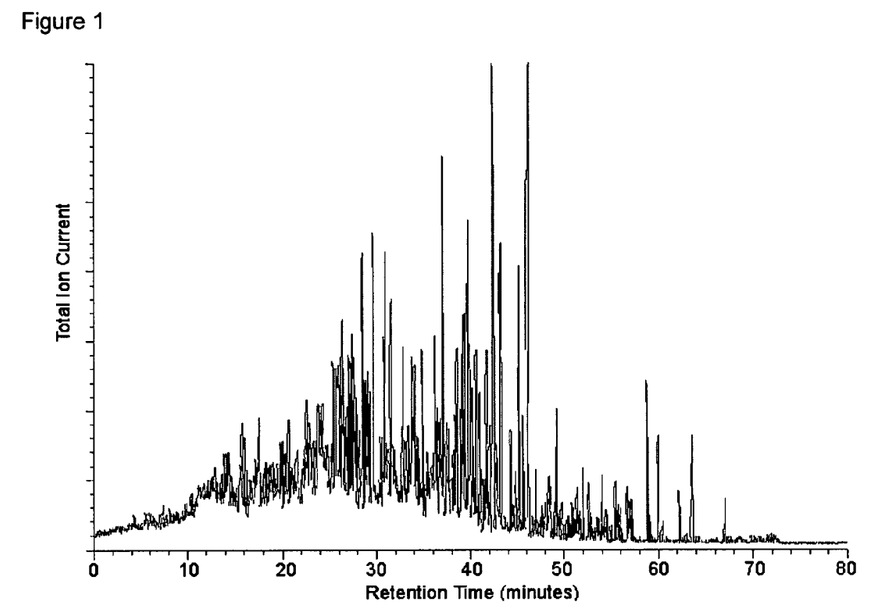
FIG. 1 shows a typical GC-MS total ion chromatogram with Field Ionization as the MS ionization mechanism.

FIG. 1 is a typical GC-MS total ion chromatogram with Field Ionization (FI) as the ionization mechanism. The X-axis is retention time or a scan number and Y-axis is total ion current (TIC). If a peak in the TIC is of interest, the MS scan corresponding to that peak can be brought up and examined to identify the chemical structure of that specific component. In this situation, the GC is used as a separation device and the MS is used as an identification apparatus. The hyphenation of GC and MS, GC-MS, provides a much more powerful instrument than GC-FID for separated component identification.

Figure 2:
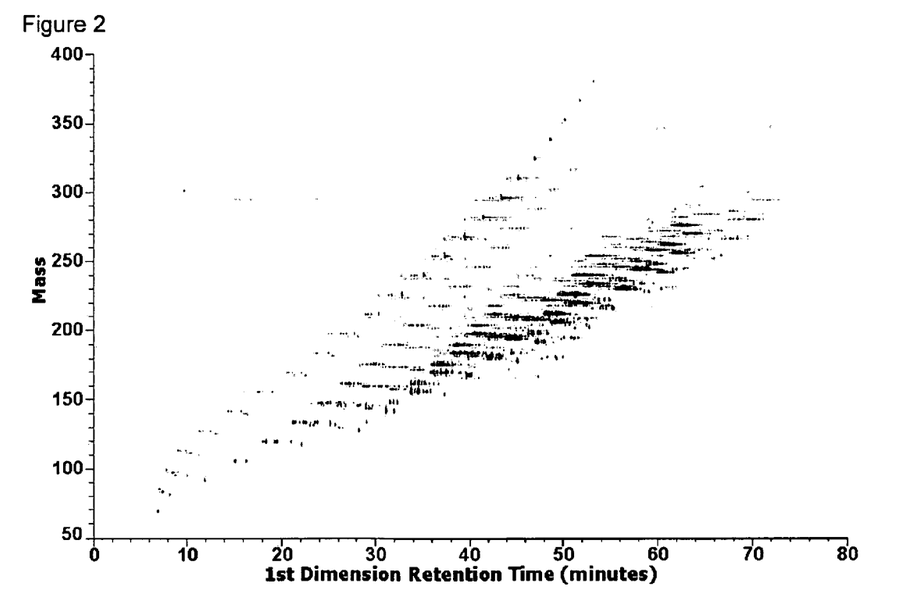
FIG. 2 shows the GC-MS three-dimensional chromatogram that all mass spectra plot in the Y-Z plan and staggered up along the X-axis.

Since every data point in FIG. 1 is a representative of an MS scan, instead of one point (TIC), the Y-axis can display the whole mass spectrum, where Y-axis becomes a mass axis, and the Z-axis is the ion intensity. This way, the GC-MS chromatogram can be turned from a two-dimensional display to a three-dimensional display. FIG. 2 shows the GC-MS three-dimensional chromatogram that all mass spectra plot in the Y-Z plan and staggered up along the X-axis. FIG. 2 is the three-dimensional chromatogram of the same sample as FIG. 1. Each component in the original mixture has a peak in FIG. 2.

Figure 3:
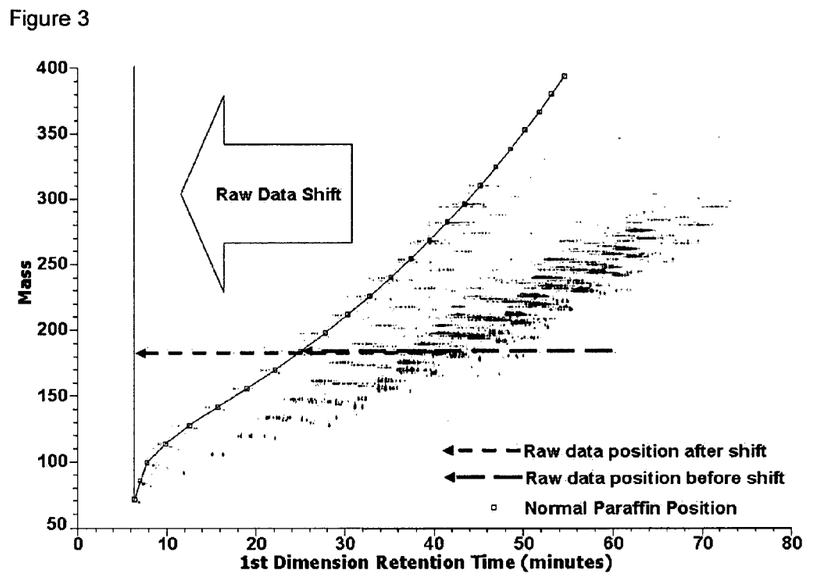
FIG. 3 shows a graphical illustration of the conversion of FIG. 2 to FIG. 4.
Figure 12:
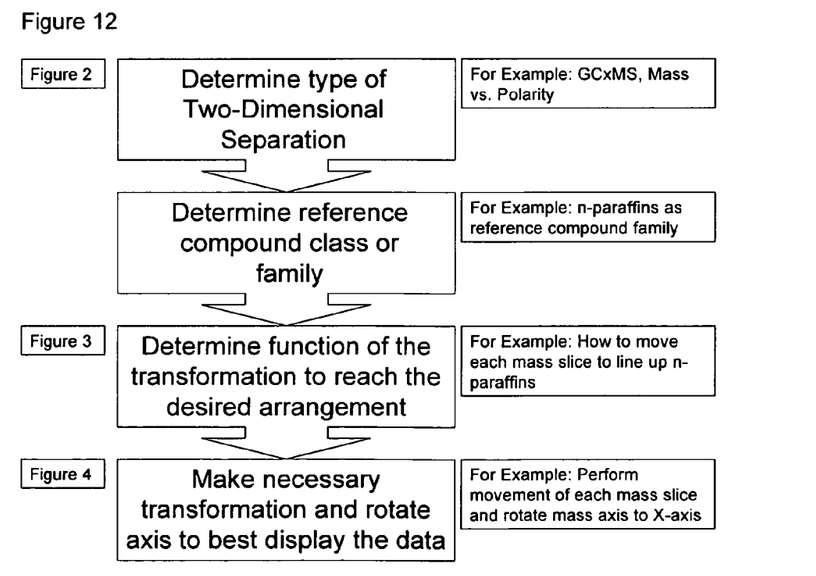
FIG. 12 is a flow chart for the algorithm for the graphical illustration of FIG. 3.

In order for a GC-MS chromatogram to show the two-dimensional separation and provide compound class information, one needs to manipulate the display to change the GC-MS to a GC×MS. During this conversion, one aspect to consider is the mass axis. It is generally true that the higher the parent mass, higher the boiling point of the molecule. Therefore the mass axis can be viewed as approximately equivalent to the boiling point axis. The other aspect is the retention time-axis, the retention time-axis is a relative polarity scale; it represents the polarity separation of each component with the same mass. In this experiment, the retention time-axis can be viewed as the relative polarity scale that reference to paraffin (or normal-paraffin). In the retention time axis of FIG. 2, each polarity slice can be rotated in such a way that the relative polarity is referenced to the normal paraffin (or lined-up along the position of normal paraffins). FIG. 3 shows a graphical illustration of the conversion of FIG. 2 to FIG. 4. FIG. 12 shows a flow chart of the algorithm for the graphical illustration of FIG. 3.

Figure 4:
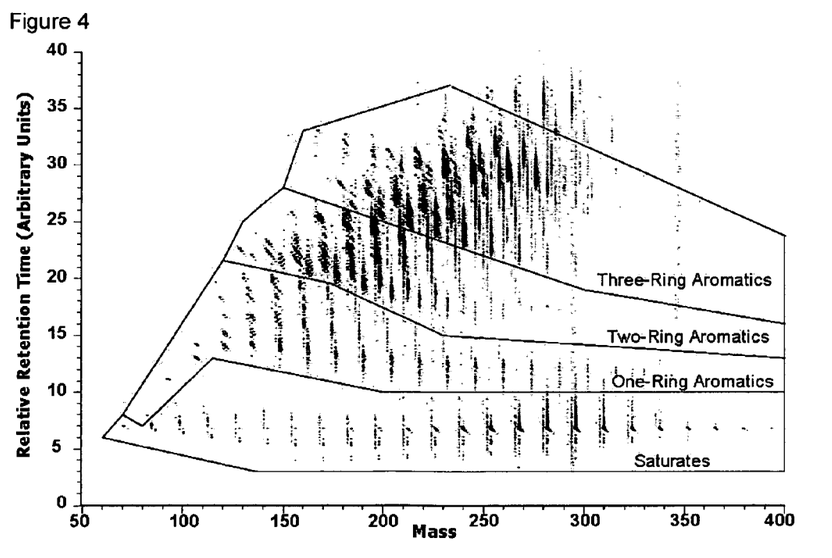
FIG. 4 shows the GC×MS three-dimensional chromatogram that was converted from the FIG. 2 through the data processing/visualization method.

After this transformation, the mass axis is rearranged as the X-axis and the Y-axis is the relative polarity axis and FIG. 2 is converted to FIG. 4. The compound classes are identified in FIG. 4 based on their two-dimensional patterns. Thus when operating the GC-MS with MS in a soft ionization mode (FI), the traditional GC-MS separation/identification of a mixture can be appropriately visualized as a two-dimensional separation (GC×MS).

Figure 5:
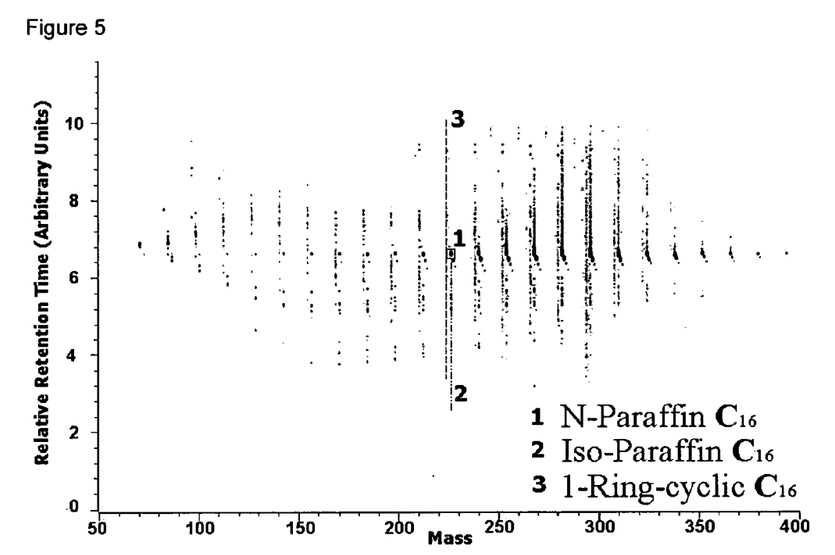
FIG. 5 shows the saturate compound class portion of this diesel mixture with detailed isomer distribution.

The three-dimensional visualization of GC×MS provides a clear separation of compound classes. However, this new visualization also gives an easy way for compound assignment/identification because each compound series can be tracked by their parent masses. FIG. 5 show the saturate compound class portion of this diesel mixture with detailed isomer distribution of each compound group in the chromatogram. The paraffins, one-ring saturated cyclic compounds and two-ring saturated cyclic compounds can be assigned by their masses. There are clear separations based on their parent mass without worry of any co-elution or interference.

Figure 6:
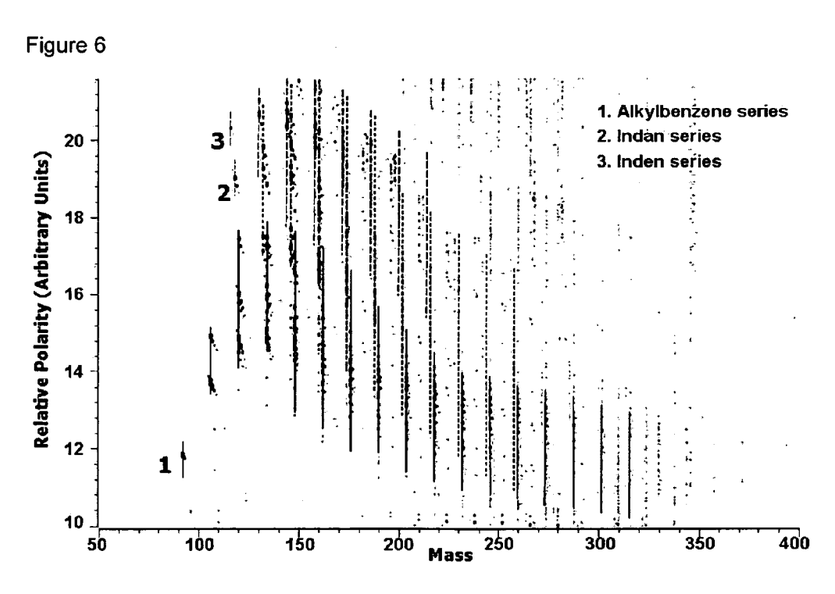
FIG. 6 shows the one-ring aromatic portion of this diesel mixture.
Figure 7:
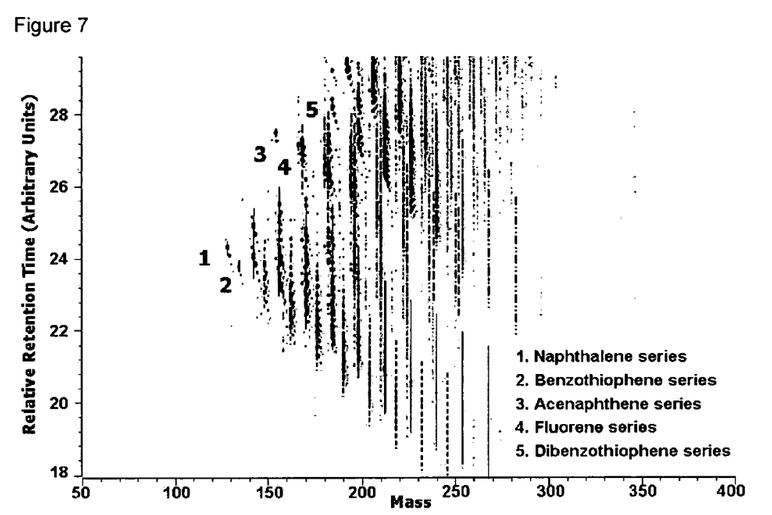
FIG. 7 shows the two-ring aromatic portion of this diesel mixture.
Figure 8:
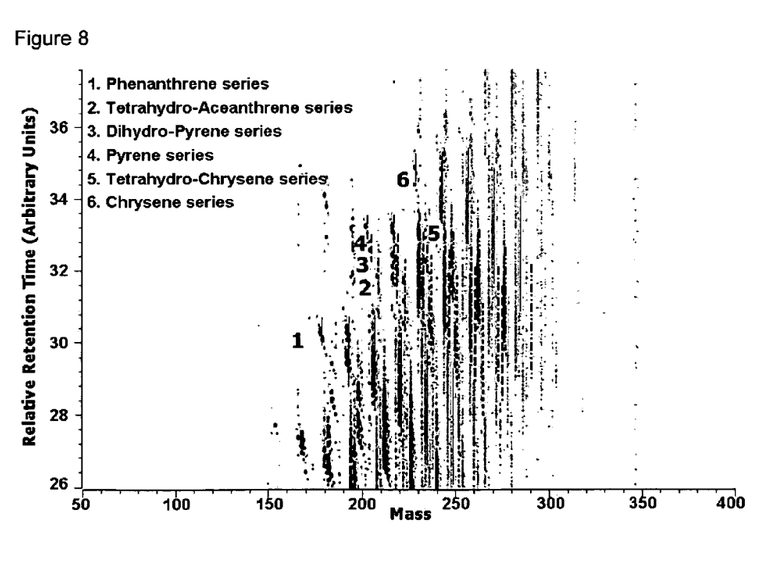
FIG. 8 shows the three-ring aromatic portion of this diesel mixture.

FIG. 6 shows the one-ring aromatic portion of this diesel mixture. There are three major compound groups identified in carbon series under this compound class. FIG. 7 and FIG. 8 show the two-ring and three-ring aromatic portions of this diesel mixture. The most abundance compound groups in these two portions are also assigned.

Discussion

Figure 9:
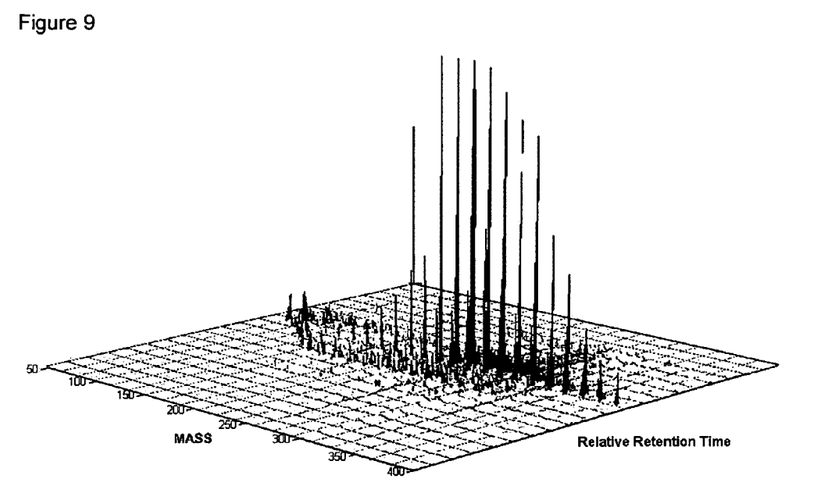
FIG. 9 shows the other visualization of three-dimensional chromatogram of the saturate portion in the diesel sample so that the relative intensities are emphasized.

This new data processing/visualization method gives a new way to treat the GC-MS data. The most valuable advantage of this method is the visualization of separated compound classes. In addition, the data can be displayed in a more intuitive way, such that either the distribution or the relative intensity is emphasized. FIG. 9 is a way to display the three-dimensional chromatogram of the saturate portion in this diesel sample so that the relative intensities are emphasized.

In additional to compound class separation, the separation of compound group within each compound class is another challenging task in petroleum separation. However, the GC×MS does a very good job in providing detailed compound group separation data. For example, in the saturates class, paraffins can be separated from one-ring saturate cyclic compounds. Another example can be found in two and three aromatic ring portions. The different compound groups can be well separated based on their parent mass.

Because the GC-MS operates in the FI mode, the parent masses of all compounds can be obtained in one experiment. The high resolution mass operation means each mass will represent a unique molecular formula. This particular feature becomes a powerful tool when looking into element specific compound distribution in the complex mixture. In the GC-MS, a specific mass or group of masses can be extracted from data to form a separate chromatogram. This operation is similar to but more advanced than signal ion monitoring in the traditional GC-MS data analysis. Sulfur containing compound chromatograms (e.g., benzothiophenes and dibenzothiophenes) and nitrogen containing compound chromatograms (indoles and carbazoles) can be extracted out from original GC×MS chromatograms to form a separate elemental specific chromatograms.

Figure 10:
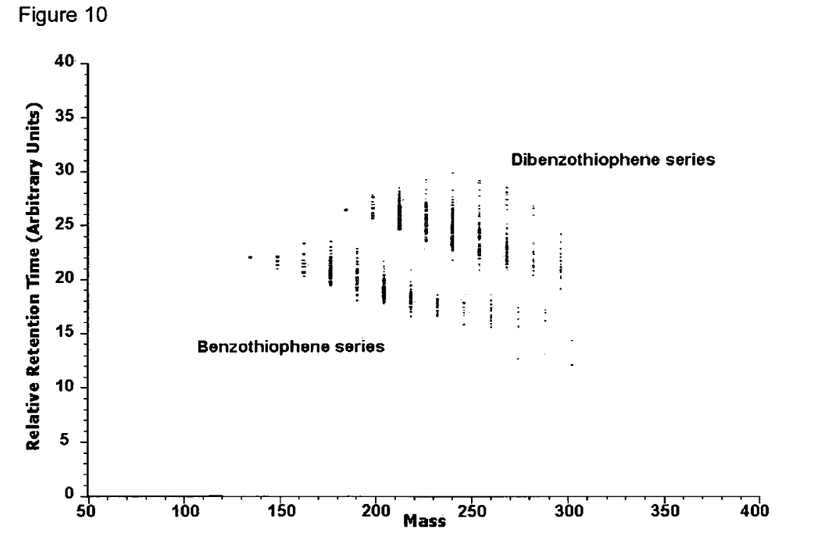
FIG. 10 shows the sulfur containing compound chromatogram (benzothiophenes and dibenzothiophenes).
Figure 11:
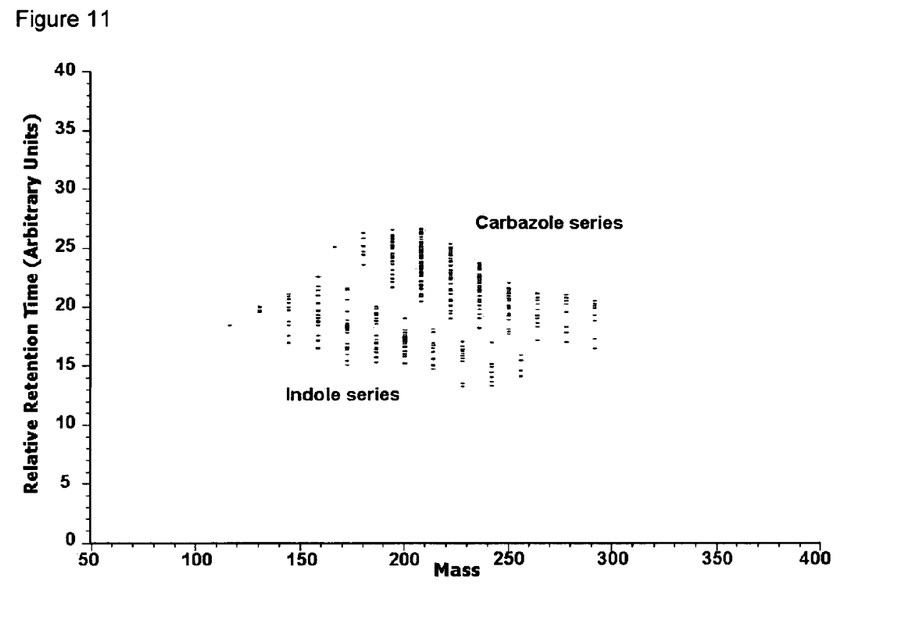
FIG. 11 shows the nitrogen containing compound chromatogram (indoles and carbazoles).

FIG. 10 and FIG. 11 illustrate the sulfur containing compound chromatogram (benzothiophenes and dibenzothiophenes) and nitrogen containing compound chromatogram (indoles and carbazoles). During this exact mass extraction process, there is interference that was caused by similar mass of hydrocarbon analogs. However, most of interference can be easily eliminated after carefully examining their compound class, relative polarity and appropriate isotopes.

The quantitative analysis of GC×MS faces the same challenge as GC-MS. Because of the non-universal response of parent ion production, it is not practical to use the parent ion intensity directly to perform the quantitative analysis. The relative response factor generation has to rely on pure compound calibration or comparison with other detector that has more universal response, such as FID.

This new data processing/visualization method can turn the GC-MS with an appropriate soft ionization mechanism, such as FI, into a two-dimensional separation technique, GC×MS. The major advantage of GC×MS is the compound class separation. The compound groups within a compound class are also well separated based on their parent masses. Because of the high resolution mass operation, the specific elemental containing compound distribution can also be generated through the extraction of specific mass groups. For qualitative analysis, GC×MS is a one-for-all technique where one experiment can generate most of the information.

What is claimed is:

1. A method for the processing and display of a two (multi) dimensional data obtained from a two (multi) "chromatographic" or "non-chromatographic" type separation system comprising a. determining appropriate the separation dimension from each separation technique
   b. referencing a compound class or compound family
   c. transforming every other separated compounds in a different separation dimension to line-up to referencing compound class or family
   d. rearranging the separation dimension axis to best display the two (multi) dimensional separation results.

2. The method of claim 1 wherein the separation dimension for "chromatographic" type separation methods that include gas chromatography (GC), liquid chromatography (LC), supercritical fluid chromatography (SFC), size exclusion chromatography (SEC) is defined in retention time (minutes) or retention time related/deviated unit (including temperature in GC, molecular solubility in LC, molecular weight in SEC).

3. The method of claim 1 wherein the separation dimension for the "non-chromatographic" spectroscopic/wavelength-type separation methods, that include X-ray, Vacuum ultraviolet (VUV), ultraviolet and visible (UV-Vis), infrared (IR), atomic absorption (AA) and atomic emission spectroscopy (AES), Fluorescence is defined in wavelength (length unit, such as nanometer (nm), angstrom (Å), or wavenumber ($cm^{-1}$), or wavelength related/deviated unit (such as energy unit, electron volts, (eV), etc.).

4. The method of claim 1 wherein the separation dimension for "non-chromatographic" mass separation methods, that include Mass Spectrometry, is defined as mass or molecular weight (Mw) or mass/molecular weight related/deviated unit (including temperature unit, and boiling point).

5. The method of claim 1 wherein the separation dimension for "non-chromatographic" type methods including thermal separation techniques, Thermalgravmetric analysis (TGA), differential scanning calorimeter (DSC), evolved gas analysis (EVA), and Pyrolysis (Py), is defined as temperature unit.

6. The method of claim 1 wherein the referencing compound class or family for "chromatographic" type separation methods that include GC, LC, SFC, and SEC, is similar in structure, similar in polarity, or similar in other physical properties which the chromatographic separation technique is based on.

7. The method of claim 6 wherein the referencing compound is the family of normal paraffins, family of linear alkyl benzene, family of linear alkyl naphthalene, or family of saturated straight chain fatty acid.

8. The method of claim 1 wherein the referencing compound for "non-chromatographic" thermal separation techniques, that include Thermalgravmetric analysis (TGA), DSC, evolved gas analysis (EVA), and Pyrolysis (Py), is the compound class or family is similar in molecular structure, similar in certain functional group in the structure, which the thermal separation technique is based on.

9. The method of claim 8 wherein the referencing compound is a family of paraffins, family of naphthenes, family of three-ring aromatics, or family of indoles.

10. The method of claim 1 wherein the referencing compound for "non-chromatographic" spectroscopic/wavelength-type separation methods, that include X-ray, Vacuum ultraviolet (VUV), ultraviolet and visible (UV-Vis), infrared (IR), atomic absorption (AA) and atomic emission spectroscopy (AES), Fluorescence, is similar in structure, similar in energy being absorbed, or similar in other intra-inter atomic and molecular energy level transition which the spectroscopic separation method is based on.

11. The method of claim 10 wherein the referencing compounds is the family of molecules with the same functional group like alpha-olefin family, family of straight chain alcohol, family of one-ring aromatics with the same ring position substitution, or family of compounds with hydrogen bonding, etc.

12. The method of claim 11 wherein the referencing compounds for "non-chromatographic" mass separation methods, Mass Spectrometry, the compound class or family is similar in molecular structure, similar in certain functional group in the structure, which the mass spectrometric separation technique is based on.

13. The method of claim 12 wherein the referencing compounds is a family of paraffins, family of olefins, family of one-ring aromatics, or family of dibenzothiophenes.

* * * * *